United States Patent [19]

Wilke et al.

[11] 4,017,526

[45] Apr. 12, 1977

[54] METAL COMPLEXES

[75] Inventors: Günther Wilke; Ernst Willi Müller, both of Mulheim (Ruhr), Germany

[73] Assignee: Studiengesellschaft Kohle m.b.H., Mulheim (Ruhr), Germany

[22] Filed: Apr. 30, 1975

[21] Appl. No.: 573,198

Related U.S. Application Data

[60] Division of Ser. No. 532,900, March 9, 1966, which is a division of Ser. No. 104,221, April 20, 1961, abandoned, and a continuation-in-part of Ser. No. 76,520, Dec. 19, 1960, abandoned, and Ser. No. 203,753, June 20, 1962, abandoned.

[30] Foreign Application Priority Data

Dec. 22, 1959 Germany .......................... 1593012
Apr. 28, 1960 Germany .............................. 16427

[52] U.S. Cl. .................... 260/439 CY; 252/431 R; 252/431 P; 260/429 R; 260/429 AR; 260/429 CY; 260/429 J; 260/438.5 R; 260/437 R; 260/270 PY

[51] Int. Cl.² .................. C07F 15/04; C07F 15/06
[58] Field of Search ............ 260/429 AR, 429 CY, 260/429 R, 439 R, 429 J, 439 CY, 438.5 R, 270 R

[56] References Cited

UNITED STATES PATENTS

| | | | |
|---|---|---|---|
| 2,953,586 | 9/1960 | Hafner et al. | 260/429 |
| 3,328,443 | 6/1967 | Clark et al. | 260/439 |

OTHER PUBLICATIONS

Malatesta et al., J. Chem. Soc., pp. 1186–1188, (1957).
Malatesta et al., J. Chem. Soc., pp. 2323–2328, (1958).

*Primary Examiner*—Helen M. S. Sneed
*Attorney, Agent, or Firm*—Burgess, Dinklage & Sprung

[57] ABSTRACT

Carbonyl-free complexes of nickel or cobalt with an olefinic compound which are useful as catalysts.

6 Claims, No Drawings

METAL COMPLEXES

This is a division of application Ser. No. 532,900, filed Mar. 9, 1966, which is a division of application Ser. No. 104,221, filed Apr. 20, 1961 now abandoned and a continuation-in-part of application Ser. No. 76,520, filed Dec. 19, 1960 now abandoned and application Ser. No. 203,753, filed June 20, 1962, now abandoned and only contains subject matters disclosed in said prior applications. The subject matter of said prior filed applications is herein incorporated by reference.

This invention relates to metal complexes. It more particularly refers to complexes between a metal of group VIII of the periodic table and an electron donating group which complex is II bonded.

Complexes of various transition metals, including those of group VIII of the periodic table, are known. An example of such a complex which contains a II bond is dibenzene chromium. This type of compound is produced by reacting chromium trichloride, aluminum chloride, metallic aluminum and benzene under pressure and at temperatures of about 150° C. The reaction product is dibenzene-chromium-I-aluminum tetrachloride which is converted to the II bonded complex dibenzene chromium by reduction, for example with nascent hydrogen.

Transition metal II bonded complexes are also produced by reacting transition metal carbonyl compounds with aromatic hydrocarbons, e.g. cobalt or iron carbonyl is reacted with benzene at elevated temperatures to displace one or more of the carbonyl groups with an aromatic group to produce a complex containing transition metal bonded to both an aromatic moiety and a carbonyl moiety.

Additionally, it is known to form olefin-carbonyl-transition metal complexes which are II bonded by reaction of olefines with metal carbonyls, e.g. nickel tetracarbonyl or ironpentacarbonyl will react with cyclooctatriene or cyclooctatraene to produce metal-carbonyl-olefin II-bonded complexes.

The processes for the production of II-complexes known in the art generally operate under rather severe reaction conditions which are often unsuited, because of their severity, to the production of the more sensitive II-complexes. Further, these prior processes often use a metal carbonyl as a reactant. This is not particularly desirable in view of the potentially injurious and harmful nature of many of the metal carbonyl compounds. Additionally, the reaction product II complexes often contain carbonyl moieties therein which is also not particularly desirable.

It is known that conjugated diolefines, such as butadiene, isoprene, piperylene and the like can be dimerized and trimerized to cyclic dienes and trienes by the action of titanium or chromium halides and organic aluminum compounds upon the conjugated diolefin at temperatures of up to about 150° C and in the presence of solvents such as aliphatic, aromatic or halogenated hydrocarbons; see U.S. Pat. No. 2,964,574 for illustrations of this subject matter.

According to German Pat. Spec. No. 881,511 and U.S. Pat. No. 2,686,209, dimerization of conjugated diolefines is catalyzed by nickel-carbonyl-organic phosphorous compound complex of the formula:

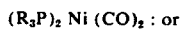

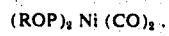

It will be appreciated that these catalysts are derived and prepared from nickel carbonyl, which is extremely toxic, and activated by pretreatment with acetylene under pressure. Reaction times of up to 100 hours have been noted to be required to produce useful conversions of the conjugated diene to its cyclic dimer or trimer when catalysts as immediately herein above defined have been used.

It is therefore an object of this invention to provide a novel group of group VIII transition metal II-bonded complexes.

It is another object of this invention to provide a novel group of group VIII transition metal II-bonded complexes which contain no carbonyl moieties in the complex.

It is a further object of this invention to provide a novel process for the production of group VIII transition metal II-bonded complexes containing no carbonyl moiety in the complex.

It is a still further object of this invention to provide a novel process of dimerizing and trimerizing conjugated diolefins using the novel complexes of this invention as catalysts for said process.

Other and additional objects of this invention will become apparent from a consideration of this entire specification including the claims appended hereto.

As used herein the term "carbonyl moiety" is intended to mean a C—O group itself as in the compound nickel carbonyl as distinguished from carbonyl containing compounds such as ketones, carboxylic acids and aldehydes.

In accord with and fulfilling these objects, this invention has as one of its aspects the provision of a group of complexes containing group VIII metals II-bonded to an electron donating group which complex contains no carbonyl moiety therein. The group VIII metals according to this invention are iron, cobalt, nickel, ruthenium, rhodium, palladium, carnium, iridium and platinum. Preferred group VIII metals are iron, cobalt and nickel, with nickel being the most preferred.

Suitable electron donors of he complex of this invention are organic compounds generally catagorized as Lewis bases. Lewis bases are those compounds having free electron pairs which are capable of acting as electron donors. These donors may contain unsaturation either in the form of olefinic or acetylenic unsaturation; they may be organic diketones. Organic compounds of metals or metalloids of group Va of the periodic table where such compound contains at least one pair of donatable unshared electrons are suitable electron donors. Such group Va metal compounds are exemplified by alkyl and aryl phosphines, phosphites, stibines, tertiary amines and araines. Organic diketones suitable for use as electron donors are exemplified by biacetyl and acetyl acetonate. Suitable unsaturated compounds include cyclic polyolefines such as cyclo-octatetraene, cyclo-octadiene and cyclododecatriene; and acetylenes such as phenyl acetylene and butyne-2. The reaction by which the complexes of the instant invention are prepared comprises mixing a group VIII transition metal compound with a suitable electron donor under reduction conditions such as in the presence of a suitable organo-metallic compound reducing agent. The reaction mixture is preferably produced as a solution or suspension as aforesaid. Heat of reaction is suitably removed by external cooling or, if the reaction medium has a sufficiently low boiling point, such heat of reaction may be removed by boiling off the reaction medium.

It is often desirable to carry out the complex formation in a reaction solvent medium. The applicable solvents are those which are substantially inert with respect to the reactant and the reaction product under the conditions of reaction and under the conditions of resolution of the reaction product. Such solvents include aromatic and saturated aliphatic and alicyclic hydrocarbons such as hexane, cyclohexane and benzene; open chain or cyclic ethers such as diethyl ether, tetrahydrofuran are also useful.

The reaction is carried out under relatively mild conditions. Temperatures of about −80° to 100° C are suitable, with temperatures of about −40° C to +5° C being preferred.

The group VIII transition metal compound reactant is suitably a salt of an organic moiety such as for example acetylacetonate, alcoholate, glyoxime, acetoacetate, etc.

The organometallic reducing agent suitably contains a metal of groups I, II or III, preferably Ia, IIa, or IIIa, of the periodic table as for example lithium, zinc, magnesium or aluminum, most preferably aluminum. The organic portion of the organometallic reducing agent is suitably an alkyl, cycloalkyl, alkoxy, aryl, aralkyl group or mixtures thereof for example ethyl, butyl, phenyl, cyclohexyl, ethoxy. It is preferred to employ an alkoxy alkyl aluminum such as ethoxydiethyl aluminum.

The group VIII metal complexes of this invention may also be prepared by a complex exchange process which can be analogized to an ester interchange reaction. Thus for example, catalysts according to this invention can be prepared by reaction between a group VIII transition metal salt and an electron donor in the presence of a reducing agent and the complex thus formed reacted with another electron donor, such a triaryl phosphite, to exchange the second electron donor ligand for the first used electron donor ligand. Exemplary of this exchange reaction is the reaction of triphenyl phosphite with bis-cyclooctadienyl nickel(o) to form triphenylphosphite nickel(o).

The materials prepared according to the practice of this invention may be used as catalysts as herein described either in the form of their preparation reaction products or as pure or relatively pure compounds.

Should it be desired to use pure compounds, the reaction products can be resolved by relatively known compound separation techniques such as distillation, sublimation, extraction, crystallization and/or washing. The choice of any particular reaction product resolution technique will depend to a great extent upon the nature, and particularly the stability, of the complex product. In general washing with water or dilute acid has been found to be an effective resolution technique.

The following Examples are given by way of illustration of the practice of this invention with respect to preparation of the novel group VIII metal II bonded complexes thereof. These Examples are illustrative of and not limiting on the scope of this invention.

EXAMPLE 1

100 gms. of nickel acetyl acetonate are dissolved under inert gas in 1 liter of absolute air-free benzene and mixed with 100 gms. of cyclooctadiene-(1,5). The solution is cooled to 0°–+5° C. and then 115 gms. of monoethoxy-diethylaluminum are added dropwise within 2 hours. The mixture is stirred for 15 hours at the same temperature. Neat yellow crystals are precipitated, which are filtered with suction and washed with small amounts of fresh benzene. Further amounts of the same substance can be isolated from the mother liquor. The yield is 100 gms. = 93.5%, based on $(C_8H_{12})_2Ni$. The result of the elementary analysis agrees with the empirical formula. The product obtained is dicyclo-octadiene-nickel-(0). The compound is sensitive to oxygen.

EXAMPLE 2

100 gms. of nickel acetyl acetonate are reacted with 115 gms. of monoethoxy-diethyl aluminum in the presence of 100 gms. of cyclooctatetraene under the conditions of Example 1. Very soon after the addition of the aluminum-organic compound, almost black-colored needles exhibiting metallic lustre precipitate from the reaction mixture. Upon completion of the precipitation of crystals, the same are filtered with suction and the sparingly soluble crystals are washed with benzene.

Yield: 38 gms. = 60% of the theoretical, based on $C_8H_8Ni$. The result of the elementary analysis agrees with this empirical formula, i.e. the compound obtained in cyclooctatetraene nickel (O). When heating the crystals, a metallic mirror is deposited on the walls of the vessel.

EXAMPLE 3

10 gms. of nickel acetyl acetonate are suspended in 200 ml. of absolute ether under argon and mixed with 30 g. of all-trans cyclododeca-(1,5,9)-triene. The mixture is cooled to −40° C. At this temperature, a solution of 11.5 gms. of aluminum trimethyl in 100 ml. of ether is added. An extremely oxygen-sensitive red solution is formed. When all of the green nickel compound has passed into solution, the ether is sucked off and the residue is distilled under high vacuum. There distils a mixture of excess cyclododecatriene and a deep red compound which, at the end of the distillation, precipitates in the colder parts of the apparatus in the form of deep red needles having metallic lustre. By heating, all of the crystals are driven over into the receiver. 30 gms. of a red-colored distillate are obtained. The content of nickel is determined in an aliquot part of the distillate. 53% of the nickel charged as acetyl acetonate are found as a red complex in the distillate. The exact composition of the new nickel compound is found to be $C_{12}H_{18}Ni$ by elementary analysis of the pure red crystals isolated by repeated distillation or sublimation. This compound is all-transcyclododeca-(1,5,9)-triene-centro-nickel-(0).

EXAMPLE 4

The procedure is the same as in Example 3 except that absolute hexane is used as the solvent. Aluminum triethyl is used as the metal alkyl. 41.7% of the nickel charged are found as complex in the distillate.

EXAMPLE 5

The procedure is the same as in Example 3 except that tetrahydrofurane is used as the solvent. Monoethoxydiethylaluminum is used as the metal alkyl. Yield, 25%.

EXAMPLE 6

10 gms. of nickel acetyl acetonate are dissolved in 100–200 ml. of benzene and mixed with 10 ml. of cyclooctadiene-(1,5). 10 gms. of monoethoxy-diethylaluminum are added to the mixture at 0° C. Before a precipitation of crystals begins, the mixture is decomposed after 2 hours with 2 N hydrochloric acid to remove the aluminum-organic compound. The deeply red-brown colored benzene solution is subsequently washed with a biocarbonate solution and then dried with air-free ignited sodium sulfate. The benzene is then removed in vacuo and the residue is recrystallized from hexane. The elementary analysis of the orange-colored crystals agrees with the formula $C_{13}H_{20}O_2Ni$.

This compound is cyclooctadiene-nickel-(0)-acetylacetone. The yield is 2.6 g. = 25% of the theoretical, based on nickel charged.

EXAMPLE 7

1 gram of nickel acetyl acetonate and 3 gms. of all-trans-cyclododeca-(1,5,9)-triene are dissolved in 20 ml. of absolute ether. The solution is mixed with 0.54 gms. of $Mg(C_2H_5)_2$ in 15 ml. of ether at −80° and warmed to room temperature. After distillation under high vacuum, the yield is determined in the distillate by analysis for nickel. 15% of the theory of trans,trans,-trans-cyclododeca-(1,5,9)-triene-centro-Ni-(0).

EXAMPLE 8

The procedure is the same as in Example 7.

1 gm. of nickel acetyl acetonate, 3 gms. of trans,-trans,trans-cyclododeca-(1,5,9)-triene, 20 ml. of absolute ether, 1 gm. of $Zn(C_2H_5)_2$ in 20 ml. of ether.

Yield: 41% of the theory of trans,trans,trans-cyclododeca-(1,5,9-triene-centro-Ni-(0).

EXAMPLE 9

The procedure is the same as in Example 7.

1 gm. of nickel acetyl acetonate, 3 gms. of trans,-trans,trans-cyclododeca-(1,5,9)-triene, 20 ml. of absolute ether, 0.27 gms. of Li—$C_2H_5$ in 10 ml. of ether.

Yield: 3% of the theory of trans,trans,trans-cyclododeca-(1,5,9)-triene-centro-Ni-(0).

EXAMPLE 10

2.45 gms. of cobalt acetyl acetonate are dissolved in 126 ml. of absolute benzene, mixed with 1.98 gms. of phenyl acetylene and, while cooling with ice, reduced with 71 ml. of a benzene solution of ethoxydiethyl aluminum containing 422 mg./ml. There is formed a black complex solution which is capable of converting butadiene into a mixture of vinyl cyclohexene, cyclooctadiene, 3-methylheptatriene and cyclododecatriene.

The aluminum can be washed out of the benzenic complex solution with 5 N hydrochloric acid. The cobalt remains in the organic phase which, after evaporation in vacuo, gives a brown-black amorphous cobalt compound.

EXAMPLE 11

The procedure is the same as in Example 10.

1.95 gms. of Fe-acetyl acetonate, 126 ml. of absolute benzene, 2.95 gms. of phenylacetylene, 71 ml. of ethoxydiethyl aluminum solution containing 422 mg./ml. give a black complex solution capable of converting butadiene into vinyl cyclohexene, cyclooctadiene, 3-methylheptatriene and cyclododecatriene.

The aluminum can be dissolved out of the benzenic complex solution by means of 5 N HCl. The iron remains in the organic phase and is obtained as a red amorphous organic compound after evaporation of the solution in vacuo.

EXAMPLE 12

The procedure is the same as in Example 10. 1 gm. of Fe-acetylacetonate, 10.3 gms. of triphenylphosphine, 50 ml of absolute benzene, 45 ml. of ethoxydiethyl aluminum solution containing 422 mg./ml. give a yellow-brown complex solution capable of converting butadiene into vinyl cyclohexene, cyclooctadiene, 3-methyl-heptatriene and cyclododecatriene.

EXAMPLE 13

The procedure is the same as in Example 10.

1 gm. of Co-acetylacetonate, 8.8 gms. of triphenylphosphine, 60 ml. of absolute benzene, 36 ml. of ethoxydiethyl aluminum solution containing 422 mg./ml. give a brown-black complex solution capable of converting butadiene into vinyl cyclohexene, cyclooctadiene, 3-methyl-heptatriene and cyclododecatriene. The complex solution gets red on contact with air.

EXAMPLE 14

10 gms. of nickel acetylacetonate and 40.95 gms. of triphenylphosphine are dissolved in 400 ml. of absolute ether and the solution is reduced with 16 ml. of ethoxydiethyl aluminum at 0° C. This results in a red-brown solution from which red-brown crystals precipitate after standing for 30 minutes. Complete precipitation of the crystals is achieved by cooling. The crystals are filtered with suction, washed with ether and dried. There are obtained 32 gms. (80% of the theoretical yield) of red-brown crystals, the elementary analysis of which agrees wit the formula $Ni(P(C_6H_5)_3)_4$. The compound is sensitive to air. When allowing oxygen to act on it, triphenylphosphine oxide is formed. The compound is capable of catalyzing the formation of cyclooctadiene from butadiene.

EXAMPLE 15

5 gms. of nickel acetylacetonate and 10.24 gms. of triphenylphosphine are dissolved in 200 ml. of absolute ether and the solution is reduced at 0° C. with 8 ml. of ethoxydiethyl aluminum. This results in the formation of a red-brown solution from which red-brown crystals precipitate after standing for 30 minutes. Processing of the mixture in the manner described in Example 14 results in 7.5 gms. (50% of the theoretical yield) of red-brown crystals, the elementary analysis of which agrees with the formula $Ni(P(C_6H_5)_3)_2$. The compound is sensitive to air. It catalyzes the formation of cyclooctadiene from butadiene.

EXAMPLE 16

5 gms. dissolved nickel acetylacetonate and 10.24 gms. of triphenylphosphine and 2.12 gms. of cyclooctadiene are dissolved in 150 ml. of absolute ether and the solution is reduced at 0° C. with 8 ml. of ethoxydiethyl aluminum. This results in a red-brown solution from which red-brown butadiene, precipitate after standing for 30 minutes. The mixture is processed in the manner described in Example 14. There are obtained 7.6 gms. (50% of the theoretical yield) of red-brown crystals, the elementary analysis of which agrees with the formula $C_8H_{12}Ni(P(C_6H_5)_3)_2$. The compound is sensitive to air and catalyzes the formation of cyclooctadiene from butadiene.

EXAMPLE 17

The procedure is the same as in Example 14 except that 12.3 gms. of nickel acetoacetate enolate are used in place of 10 gms. of nickel acetylacetonate and 30 gms. (75% of the theoretical yield) of the complex described in Example 14 are obtained.

EXAMPLE 18

The procedure is the same as in Example 14 except that 11.4 gms. of nickel-bis-dimethyl glyoxime are used in place of 10 gms. of nickel acetylacetonate. The reaction which proceeds somewhat slower than in Example 14 results in 26 gms. (65% of the theoretical yield) of the complex described in Example 14.

EXAMPLE 19

The procedure is the same as in Example 14 except that 5.75 gms. of finely ground nickel formate are used in place of 10 gms. of nickel acetylacetonate. The reaction which has a somewhat slower rate than in Example 14 results in 20.5 gms. (50% of the theoretical yield) of the complex described in Example 14.

EXAMPLE 20

The procedure is the same as in Example 15 except that 10.24 gms. of triphenylphosphine and 3.5 gms. of transtilbene are added to the solution of nickel acetylacetonate in ether. The reduction results in the formation of a voluminous yellow-brown colored precipitate which, after standing for several days under ether, is converted into dark red crystals, the composition of which corresponds to the formula $C_{14}H_{12}Ni(P(C_6H_5)_3)_2$.

Yield: 13.4 gms. = 90% of the theoretical.

EXAMPLE 21

The procedure is the same as in Example 15 except that only 10.5 gms. of trans-stilbene are used as the donator. The reduction results in the formation of a red-brown solution from which brown crystals precipitate, the composition of which corresponds to the formula $Ni(C_{14}H_{12})_3$.

Yield: 5.8 gms. = 50% of the theoretical.

EXAMPLE 22

The procedure is the same as in Example 15 except that 11 gms. of phosphorous acid tripiperidide are used as the donator and 250 ml. of pentane are used in place of ether. After the reduction, the pentane solution is allowed to stand for 1 week at −16° C. There are obtained yellow crystals, the composition of which corresponds to the formula $Ni(P(NC_5H_{10})_3)_2$.

Yield: 3.7 gms. = 30% of the theoretical.

EXAMPLE 23

The procedure is the same as in Example 10 except that 5 gms. of purest cobalt-II-acetylacetonte, 2.5 gms. of triphenylphosphine, 100 ml. of absolute benzene, and 6 ml. of ethoxy-diethyl aluminum are used. Dark green crystals the composition of which corresponds to the formula $Co(P(C_6H_5)_3)_4$ have precipitated after 24 hours.

Yield: 16.2 gms. = 75% of the theoretical.

EXAMPLE 24

The procedure is the same as in Example 23 except that 4 gms. of cyclooctatetraene are used as the donator. Dark brown powders the composition of which corresponds to the empirical formula $Co(C_8H_8)_x$ wherein $x$ has a value from 1 to 2 depending upon the reaction temperature are obtained in yields of about 50% of the theoretical.

EXAMPLE 25

35 ml. of cyclooctatetraene and 28 ml. of aluminum triethyl are dissolved in 100 ml. of absolute benzene. Then 8.5 ml. of titanium tetrabutylate dissolved in 25 ml. of absolute benzene are added at 80° C. within 2 hours. The mixture is stirred for additional 15 hours at 80° C. After cooling, the crystals formed are separated. Black crystals having metallic lustre and corresponding to the composition of $Ti_1(C_8H_8)_4$ are obtained in a yield of 5.5 gms. corresponding to 85% of the theoretical.

EXAMPLE 26

The procedure is the same as in Example 25 except that 50 ml. of benzene, 3.3 ml. of cyclooctatetraene, 17 ml. of aluminum triethyl, and 4.2 ml. of titanium tetrabutylate dissolved in 12.5 ml. of benzene are used. There are obtained 1.8 gms. = 70% of the theory of fine yellow crystals, the composition of which corresponds to the formula $Ti_2(C_8H_8)_3$.

EXAMPLE 27

To 2.7 gms. of the complex prepared in Example 26 are added 50 ml. of cyclooctatetraene and the mixture is heated at 80° C. for 45 hours while stirring. There are obtained 2.45 gms. =73% of the theory of the complex described in Example 25.

EXAMPLE 28

The procedure is the same as in Example 14 except that 1 gm. of palladium acetylacetonate, 3.5 gms. of triphenylphosphine, 2.4 ml. of ethoxy-diethyl aluminum and 40 ml. of absolute benzene serving as the solvent are used. The reaction product is a yellow powder, the composition of which corresponds to the formula $Pd(P(C_6H_5)_3)_4$.

EXAMPLE 29

The procedure is the same as in Example 14 except that 5 gms. of nickel acetyl acetonate, 27.7 gms. of triphenylstibine, 12 ml. of ethoxy-diethyl aluminum and a mixture of 100 ml. of absolute benzene and 300 ml. of absolute ether serving as the solvent are used. Yellow-green crystals the composition of which corresponds to the formula $Ni(Sb(C_6H_5)_3)_4$ are separated after 3 hours.

EXAMPLE 30

The procedure is the same as in Example 14 except that 2.5 gms. of nickel acetylacetonate, 12 gms. of triphenylarsine, 6 ml. of ethoxy-ethyl aluminum, and a mixture of 80 ml. of absolute benzene and 100 ml. of absolute ether serving as the solvent are used. Yellow-brown crystals the composition of which corresponds to the formula $Ni(As(C_6H_5)_3)_4$ are separated after 4 hours.

EXAMPLE 31

The procedure is the same as in Example 23 except that the reduction is effected with only 1.49 ml. of ethoxydiethyl aluminum. A turquoise-colored powder the composition of which corresponds to the formula $Co(C_5H_7O_2)(P(C_6H_5)_3)$ separates in a yield of 6.6 gms. corresponding to 50% of the theoretical.

One of the important attributes of this invention is the fact that the II-bonded metal complexes referred to above are excellent catalysts for dimerizing and trimerizing conjugated diolefins such as butadiene, isoprene or piperylene. This dimerization and/or trimerization process is suitably carried out by mixing a conjugated diene with catalyst solution, either as a pure or relatively pure compound or as an unresolved preparation reaction mixture, prepared as aforesaid under pressure. The reaction mixture is heated to sustain the reaction after which the reaction product is resolved. Suitably the reaction is carried out at about 2 to 20 atmospheres pressure and about 20° to 150° C. The reaction temperature is preferably about 60° to 100° C.

The conjugated diene reactant may be introduced into the reaction mass as a pure material but it is also within the scope of this invention to employ mixed reactant streams, that is those containing the reactant admixed with other materials which are not particularly affected under the reaction conditions. Thus, butadiene may be fed as a mixture thereof with butanes and/or butenes such as for example the product stream from a $C_4$ dehydrogenation reaction for the production of butadiene.

The reaction products are predominantly seven(7), eight(8) and twelve(12) membered diolefinally unsaturated ring compounds.

Depending on the choice of the transition metal, the electron donor and the molar ratio between transition metal and organometallic component and electron donor, catalysts are formed, as further explained in the examples below, which permit the formation from butadiene of either cyclooctadi- 1,5-ene as well as relatively small quantities of vinyl cyclohexene or trans, trans, trans-cyclododecatri-1,5,9-ene as well as traces of trans,trans,cis-cyclododecatri-1,5,9-one as principal product, or mixtures of the said compounds. The cyclic dimers or trimers are formed in particularly high yields when using nickel compounds. On the other hand, if iron compounds are used, the 5-methyl-heptatri-1,3,6-ene is obtained as principal product. It is particularly advantageous to use for the production of the catalysts those compounds of transition metals which have good solubility in the solvents being employed, but catalysts can also be obtained from compounds which are sparingly soluble in the solvents, only in these cases the formation of the catalysts from its components takes a considerably longer time. For this reason, transition metal compounds which have proved especially suitable according to the process of the invention are those in which the transition metal atoms are linked to organic radicals, such as acetyl acetonates, acetoacetic ester enolates, alcoholates, salts of weak organic acids or dimethyl glyoxime compounds.

The compounds obtained according to the process of the invention are valuable starting products for further synthesis reactions; for example, cyclooctadi-1,5-ene may be used for obtaining suberic acid or the corresponding 9-membered lactam, cyclododecatri-1,5,9-ene may be used for obtaining dodecanic diacid or the 13/membered lactam. Both the dicarboxylic acids and the lactams are valuable monomers for the production of polyesters or polyamides. Styrene is obtained from vinyl cyclohexene by dehydrogenation.

It has now surprisingly been found to be possible to make cyclooctadi-1,5-ene the main product, apart from relatively small quantities of 4-vinyl cyclohexene, by using the new catalysts having a specific composition. On the other hand, it is also possible to make cyclododecatri-1,5,9-ene the main product, but this is formed qite unexpectedly as practically pure trans,-trans,trans-cyclododecatri-1,5,9-ene practically pure trans,trans,trans-cyclodudecatri-1,5,9-ene when using the new catalysts.

The following Examples are given by way of illustration of but are not limiting on the scope of this invention.

EXAMPLE 32

1 G. of nickel acetylacetonate together with 8 g. of triphenyl phosphine (molar ratio Ni : P = 1:8) are dissolved in 60cc. of absolute benzene with heating. The mixture is cooled with iced water and 35.5 cc. of a benzene solution of ethoxydiethyl aluminium (422 mg./cc.) are slowly added. A reddish-brown solution is formed, which is introduced with exclusion of air into a 2-liter stainless steel autoclave equipped with a magnetic stirrer mechanism. 125 G. of liquid butadiene are forced into the mixture under pressure. The autoclave is heated to 80° C. and the contents are stirred until the pressure has fallen to about 2 atm., and another 125 g. of butadiene are then introduced under pressure. The reaction is completed after a total period of 5 hours, the reaction of the butadiene being quantitative. The autoclave contents are then discharged and freed by steam distillation from the catalyst and non-volatile fractions. The distillate is separated by careful fractionation into the components. The precise composition of the distillate obtained by steam distillation is determined by gas chromatographic analysis. The non-volatile constituents are disslved in benzene, separated from the catalyst residue and weighed after distilling off the benzene. The following products were obtained : 76 g. of 4-vinyl cyclohexene = 30.4% of the reacted butadiene, 156 g. of cyclooctadi-1,5-ene = 62.5% of the reacted bitadiene, 9 g. of cyclododecatri-1,5,9-ene = 3.6% of the reacted butadiene and 9 g. of non-volatile fractions = 3.6% of the reacted butadiene. The total yield of both dimers and the cyclododecatri-1,5,9-ene is 96.4 % of the reacted butadiene.

EXAMPLES 33-38

The following experiments were carried out according to Example 32, but the molar ratios of Ni:Al:P and the temperature are varied as indicated in Table 1. In each case, the catalyst is prepared from 1 g. of nickel acetylacetonate and 250 g. of butadiene are introduced.

Table I.

| No. | Ethoxy diethyl aluminium | Triphenylphosphene | Temp/Conversion | | Vinyl cyclohexene | Cyclo octadi-l, 5-ene | Cyclo dodecatri-1,5,9-ene | Non volatile fractions. |
|---|---|---|---|---|---|---|---|---|
| | | | | % of reacted butadiene. | | | | |
| 33 | 30 | 8 | 80° | 98.2 | 30.5 | 62.5 | 3.3 | 3.7 |
| 34 | 30 | 4 | 80° | 96.3 | 23.1 | 67.1 | 7.7 | 2.1 |
| 35 | 30 | 2 | 80° | 94.2 | 17 | 65 | 16.2 | 1.8 |
| 36 | 30 | 0.5 | 80° | 92.2 | 9 | 47.3 | 41.0 | 2.6 |
| 37 | 6 | 20 | 80° | 98.7 | 34.1 | 61.3 | 1.4 | 3.2 |
| 38 | 6 | 2 | 90° | 80.9 | 21.1 | 53.5 | 24.6 | 0.7 |

EXAMPLES 39–46

The following examples are carried out in accordance with Example 32 except that different organometallic components or metal hydrides and different types of solvents are employed. 1 G. of nickel acetylacetonate and 8 g. of triphenyl phosphine are used in each case for the preparation of the catalyst, and 250 g. of butadiene is employed in each case.

Table II.

| No. | Reducing agent mol/mol Ni | Conversion % | Vinyl cyclohexene | Cyclo octadi-,5-ene | Cyclo dodecatri-1,5,9-ene | Non volatile functions. |
|---|---|---|---|---|---|---|
| | | | % of reacted butadiene. | | | |
| 39 | 30 Al(C$_2$H$_5$)$_3$ | 99 | 41.3 | 15.8 | 9.0 | 32.8 |
| 40 | 30 Al(C$_2$H$_5$)$_2$H | 91 | 40.2 | 30.1 | 7.5 | 22 |
| 41 | 30 Ga(C$_4$H$_9$)$_3$ | 100 | 19.4 | 64.6 | 12.0 | 4 |
| 42 | 30 C$_2$H$_5$MgBr | 100 | 21.9 | 34.2 | 2.1 | 29.6 |
| 43 | 5 LiAlH$_4$ | 99.6 | 22.4 | 69.7 | 2.7 | 5.2 |
| 44 | 5 LiAlH$_4$ | 91 | 29.2 | 64.6 | 4.5 | 1.7 |
| 45 | 30 C$_6$H$_5$MgBr | 86 | 20 | 49.2 | 1.6 | 26 |
| 46 | 30 Zn(C$_2$H$_5$)$_2$ | 92.2 | 28.1 | 48.3 | 1.2 | 15.2 |

The solvent use for examples 39–41 and 46 is benzene, that for examples 42, 43 and 45 ether and for example 44 is tetrahydrofuran.

EXAMPLES 47–52

The following Examples are carried out according to Example 32, except that the triphenyl phosphine is replaced by varying quantities of phenyl acetylene as electron donor. The catalysts are prepared in each case from 1 g. of nickel acetylacetone and from varying quantities of ethoxy diethyl aluminum. 250 G. of butadiene are used in each case.

Table III.

| No. | Ethoxy-Diethyl-aluminium | Phenyl-acetylene | Conversion | Vinyl cyclohexene | cyclo octadi-1, 5-ene | Cyclo dodecatri-1,5,9-ene | Non volatile fractions. |
|---|---|---|---|---|---|---|---|
| | | | | % of reacted butadiene. | | | |
| 47 | 1.5 | 16 | 7.6 | 17.8 | 1.1 | 11.6 | 68.7 |
| 48 | 6 | 16 | 89 | 3.2 | 3.0 | 77.6 | 10.2 |
| 49 | 9 | 8 | 30.8 | 5.2 | 2.7 | 88.8 | 3.3 |
| 50 | 30 | 4 | 99 | 8.2 | 23.9 | 62.2 | 4.0 |
| 51 | 120 | 40 | 24.3 | 8.7 | 1.8 | 61.8 | 22.7 |
| 52 | 30 | — | 58.5 | 10.5 | 24.9 | 57.8 | 6.8 |

EXAMPLE 53

The catalyst is prepared as in Example 32, but a reaction mixture of 51.9% of butadiene and 48.1% of 1-butene is employed. 440 G. of this gas mixture are reacted in two parts over 4 hours at 80° C. The unreacted gas is blown off and condensed. 208 G. of practically pure 1-butene, that is to say, 98.5% of the 1-butene introduced is obtained. The reaction product is worked up according to Example 32. It has the following composition 3.9% of vinyl cyclohexene, 89.5% of cyclooctadi-1,5-ene, 2.6% of cyclododecatri-1,5,9-ene and 2% of non-volatile fractions. Together it amounts to 220g (corresponding to 97% of the reacted butadiene).

EXAMPLE 54

The reaction is carried out in accordance with Example 1 or Example 92, but using cobalt acetylacetonate as transition metal component. 5.9% of the butadiene used are reacted at 80° C over 16 hours. The reaction product has the following composition: 30.6% of vinyl cyclohexene, 18.6% of cyclooctadi-1,5-ene, 6.7% of 5-methyl heptatri-1,3,6-ene, 1.7% of cyclododecatri-1,5,9-ene and 42.4% of non-volatile fractions.

EXAMPLE 55

1 G. of nickel acetylacetonate is dissolved together with 2.05 g. of triphenyl phosphine in 60 cc. of absolute benzene and 40 cc. of a solution of ethoxy diethyl aluminium (280 mg./cc.) are added thereto. The reddish-brown catalyst solution is reached according to Example 32 with butadiene, a total of 0.9 kg. of butadiene being reacted over 36 hours at 80°C. The reaction product consists of: 114 g. = 12.6% of vinyl cyclohexene, 520 g. = 57.8% of cyclooctadi-1,5-ene, 255 g. = 28.3% of cyclododecatri-1,5,9-ene and 10 g. = 1.1% of non-volatile fractions.

EXAMPLE 56

The catalyst is prepared as in Example 32, but there is used in the reaction a mixture (such as directly formed by the dehydrogenation of butane) consisting of 56.6% of n-butane 27.3% of butene, 13% of butadiene and 3% of ethylene and ethane. 1.1 Kg. of the mixture are reacted over 2 hours at 100° C. The unreacted gas is discharged while hot and condensed. 950 G. of a mixture of 66.2% of n-butane, 30.2% of butene, 2.5% of ethylene and ethane and 0.2% of benzene are obtained. The reaction product is worked up according to Example 1. 143 G. are obtained, corresponding to a 100% conversion, consisting of 16.7% of vinyl cyclohexene, 68.3% of cyclooctadiene, 9.4% of n-$C_{12}$ hydrocarbon, 4.3% of cyclododecatriene and 1.3% of nonvolatile fractions.

EXAMPLES 57, 58, 59

The following Examples are carried out according to Example 32, but the nickel acetylacetonate is replaced by nickel dimethyl glyoxime (57), nickel formate (58) and nickel dicyclopentadienyl (59). The catalysts are prepared from 1 g. of nickel compound and the quantity of reducing agent indicated and each is reacted with 250 g. of butadiene at 80° C. over 10 hours.

Å represents ethoxydiethyl alumininum and Li represents lithium aluminium hydride.

Table IV

| | | | % of reacted butadiene. | | | |
|---|---|---|---|---|---|---|
| No. | Reducing agent mol/mol Ni | Triphenyl phosphine | Conversion % | Vinyl cyclohexene | Cyclo octa-di-1,5-ene | Cyclo$^{(1)}$ dodecatri-1,5,9-ene | Non volatile fractions |
| 57 | 30:1 (A) | 2 | 49.7 | 11.0 | 58.3 | 26.2 | 4.5 |
| 58 | 6:1 (A) | 2 | 79.5 | 12.5 | 69.9 | 14.4 | 3.2 |
| 59 | 4:1 (Li) | 2 | 30.2 | 17.9 | 60.0 | 16.5 | 5.6 |

$^{(1)}$n-$C_{12}$ hydrocarbon+

EXAMPLES 60–71

Examples 60 to 71 are carried out in accordance with Example 32, but using different donors. The donor used for Example 60 is methoxy vinyl acetylene and that for Example 61 phosphorus acid trimorpholide. In Example 62 cyclododecene is used as electron donor. The electron donors for Examples 63–71 are as follows:

Example 63 $N(C_2H_5)_3$, Example 64 $P(C_2H_5)_3$, Example 65 $As(C_2H_5)_3$, Example 66 $Sb(C_2H_5)_3$, Example 67 $Bi(C_2H_5)_3$, Example 68 $N(C_6H_5)_3$, Example 69 $As(C_6H_5)_3$, Example 70 $Sb(C_6H_5)_3$ and Example 71 $Bi(C_6H_5)_3$. Each of the catalysts is prepared from 1 g. of nickel acetylacetonate, the quantity indicated of othoxy diethyl aluminium and 4 mols of the donor indicated in benzene as solvent. 250 G. of butadiene is reacted at 80° C. in each case.

Table V.

| | | | | % of the reacted butadiene | | | |
|---|---|---|---|---|---|---|---|
| No. | Reducing agent mol/mol Ni | Reaction time hrs. | Conversion | Vinyl cyclohexene | Cyclo-octadiene | Cyclo$^{(1)}$ dodecatriene | Non volatile fractions. |
| 60 | 6:1 | 16 | 80.5 | 8.3 | 7.2 | 76.7 | 7.8 |
| 61 | 6:1 | 17 | 64.3 | 10.2 | 78.4 | 6.2 | 5.2 |
| 62 | 4:1 | 2 | 92.3 | 4.6 | 3.5 | 78.0 | 13.9 |
| 63 | 6:1 | 18 | 13.3 | 17.2 | 1.0 | 1.0 | 80.8 |
| 64 | 6:1 | 16 | 13.8 | 20.0 | 55.0 | 7.0 | 18.0 |
| 65 | 6:1 | 22 | 30.4 | 16.8 | 17.1 | 55.7 | 10.4 |
| 66 | 6:1 | 20 | 58.2 | 7.3 | 15.4 | 73.3 | 4.0 |
| 67 | 6:1 | 16 | 83.3 | 5.3 | 12.2 | 80.0 | 2.5 |
| 68 | 6:1 | 16 | 28.7 | 9.2 | 0.2 | 86.3 | 3.1 |
| 69 | 6:1 | 11 | 100 | 5.3 | 10.6 | 80.5 | 3.6 |
| 70 | 6:1 | 16 | 92.7 | 4.5 | 13.9 | 89.8 | 2.8 |
| 71 | 6:1 | 22 | 7.9 | 26.1 | 3.8 | 45.1 | 25.0 |

$^{(1)}$ n-$C_{12}$hydrocarbon +

EXAMPLES 72 to 78

The following Examples are carried out according to Example 32, but the reaction temperature is varied. Each of the catalysts is prepared from 1 g. of nickel acetylacetonate, 10 mols of ethoxy diethyl aluminium per mol of nickel and 4 mols of triphenyl phosphine per mol of nickel and each is reacted with 200 g. of butadiene.

Table VI.

| No. | Temp. | Time hours | Conversion | Vinyl cyclohexene | Cyclo-octadiene | Cyclo-dodecatriene | $^{(1)}$Non volatile fractions |
|---|---|---|---|---|---|---|---|
| 72 | 70 | 22 | 99.7 | 25.0 | 67.1 | 6.9 | 1.0 |
| 73 | 100 | 1 | 73.0 | 21.0 | 69.3 | 8.4 | 1.3 |
| 74 | 100 | ¾ | 93.3 | 18.8 | 70.4 | 9.3 | 1.5 |
| 75 | 125 | 1 | 84.0 | 26.6 | 63.6 | 8.3 | 1.5 |
| 76 | 130 | ¾ | 92.6 | 20.3 | 63.6 | 6.2 | 9.9 |
| 77 | 160 | ¾ | 81.3 | 20.8 | 63.2 | 6.3 | 9.7 |
| 78 | 180 | ¾ | 63.9 | 31.4 | 40.9 | 3.2 | 24.4 |

$^{(1)}$n-$C_{12}$hydrocarbon +

EXAMPLES 79 to 82

The following Examples are carried out according to Example 32, but the reaction temperature is varied.

The catalyst is prepared as in Examples 72 to 78, but the triphenyl phosphine is replaced by phosphorus acid trimorpholide.

Table VII

| No. | Temp. °C. | Time hours | conversion % | Vinyl cyclo-hexene | Cyclo-octa-diene | Cyclo[2] dodeca-triene | Non-volatile fractions |
|---|---|---|---|---|---|---|---|
| 79 | 60 | 12 | 71.6 | 35.6 | 59.6 | 3.7 | 1.7 |
| 80 | 95 | 4 | 73.8 | 17.6 | 72.8 | 7.3 | 2.3 |
| 81 | 128 | ¼ | 69.8 | 25.6 | 68.7 | 3.9 | 1.8 |
| 82 | 150 | ⅓ | 67.0 | 23.6 | 59.2 | 9.7 | 7.5 |

[2] n-$C_{12}$ hydrocarbon +

EXAMPLES 83 to 85

The following Examples are carried out according to Example 32, but the reaction temperature is varied. The catalysts are prepared as in Examples 72 to 78 but phenyl acetylene is used instead of triphenyl phosphine.

Table VIII.

| No. | Temp °C | Time hours | Conversion | Vinyl cyclo-hexene | Cyclo-octa-diene | Cyclo-dodeca-triene | n-$C_{12}$-hydro-carbon | Non-volatile fractions. |
|---|---|---|---|---|---|---|---|---|
| 83 | 110 | 4 | 93.0 | 6.4 | 15.9 | 68.0 | 7.8 | 1.9 |
| 84 | 140 | 1 | 87.5 | 9.0 | 11.7 | 60.7 | 10.4 | 8.2 |
| 85 | 175 | ⅔ | 93.0 | 12.0 | 10.0 | 36.2 | 8.8 | 33.0 |

EXAMPLE 86

5.75 G. of the complex having the formula Ni(P($C_6H_5$)$_3$)$_4$ are dissolved in 50 cc. of absolute benzene and 300 g. of butadiene are reacted therewith at 106° C. over 1½ hours. The reaction product is worked up according to Example 32. 291 G. (97% of the theoretical) are obtained containing 18.8% of vinyl cyclohexene, 59.3% of cyclooctadiene, 10.0% of cyclododecatriene, 3.9% of n-$C_{12}$-hydrocarbon and 8% of non-volatile fractions.

EXAMPLE 87

The operation is carried out as in Example 86, but using 4 g. of bis-triphenyl phosphine-nickel cyclooctadiene-(O), (($C_6H_5$)$_3$P)$_2$Ni$C_8H_{12}$, dissolved in 50 cc. of absolute benzene as catalyst. 200 G. of butadiene are reacted over 1 hour at 100° C. 200 G. (100% of the theoretical) of reaction product are obtained consisting of 26.1% of vinyl cyclohexene, 62.2% of cyclooctadiene, 7.5% of cyclododecatriene and 4.1% of n-$C_{12}$-hydrocarbon.

EXAMPLE 88

The procedure of Example 86 is used, but employing 4 G. of bis-triphenyl phosphine nickel-(O), (($C_6H_5$)$_3$P)$_2$Ni, dissolved in 50 cc. of absolute benzene as catalyst. 200 G. of butadiene are reacted over 2 hours at 100° C and 182 g. (91% of the theoretical) of reaction product are obtained consisting of 29% of vinyl cyclohexene, 62.4% of cyclooctadiene, 7.2% of cyclododecatriene and 1.4% of n-$C_{12}$-hydrocarbon.

EXAMPLE 89

This example is effected as Example 86, but using 7 g. of bis-cyclooctadiene-nickel-(O), dissolved in 100 cc. of absolute benzene as catalyst. 200 G. of butadiene are reacted within 12 hours at 100° C. and 94 g. = 47.2% of the theoretical of a reaction product are obtained, which contains 8.5% of vinyl cyclohexene, 17.4% of cyclooctadiene, 66.3% of cyclododecatriene, 4.1% of open-chain $C_8$-hydrocarbons and 3.7% of open-chain $C_{12}$-hydrocarbons.

EXAMPLE 90

3 G. of nickel acetylacetonate and 25 g. of triphenyl phosphine are dissolved in 250 cc. of benzene. This solution has added thereto, while cooling, a solution of ethoxydiethyl aluminium in benzene, which contains 350 m.mol of the aluminium compound. 100 G. of piperylene are heated in an autoclave for 36 hours to 120° C using this catalyst solution. With a conversion of 70%, there are obtained 40–45 g. of a mixture of 2-dimethyl-cyclooctadienes of boiling point 90 108°–109° C. and $n_D^{20}$ = 1.4811, which consists of about 60% of 3,7-dimethylcyclooctadi-1,5-ene and about 40% of 3,4-dimethylcyclooctadi-1,5-ene.

EXAMPLE 91

The catalyst is prepared as in Example 90 and heated together with 300 g. of isoprene in an autoclave for 12 hours to 80° C. There are obtained 15 g. of paradiprene, 20 g. of dipentene and 80–90 g. of a mixture of 2-dimethylcyclooctadienes of the boiling point 90 124°–125° C. and $n_D^{20}$ = 1.4890, which is composed of about 70% of 2,6-dimethyl-cyclooctadi-1,5-ene and about 30% of 2,5-dimethyl cyclooctadi-1,5-ene. The conversion amounts to 70–80%.

It has additionally been found to be possible to produce a hitherto unknown dimer of butadiene, the constitution of which has been recognized as that of 5-methyl-heptatri-1,3,6-ene, this substance having a boiling point at 115° C./745 mm. Mg. and a refractive index at $n_D^{20}$ of 1.4632.

EXAMPLE 92

1 G. of iron acetylacetonate is dissolved together with 8 g. of triphenyl phosphine in 60 cc. of benzene and reacted with 35.5 g. of the ethoxydiethyl aluminium solution specified in Example 1. A reddish-orange solution is formed. A total of 250 g. of butadiene is heated with the catalyst solution for 16 hours to 80° C. The reaction product is worked up as described in Example 32. It amounts to 61 g. (24.3% of the butadiene introduced) and has the following composition: 30% of vinyl cyclohexene, 1.5% of cyclooctadi- 1,5-ene, 42% of 5-methyl heptatri-1,3,6-ene and 19.7% of non-volatile fractions. The 5-methyl-heptatri-1,3,6-ene boils at 115°–115.5° C./745 mm. Hg. and has a refractive index $n_D^{20} = 1.4632$.

With catalytic hydrogenation, the quantity of hydrogen equivalent for 3 double bonds is taken up. The hydrogenation product is identical with 5-methyl heptane. 5-Methylheptatriene adds 1 mol of maleic acid anhydride. By saponification the corresponding dicarboxylic acid with the melting point 173°–175° C. is obtained.

An improvement in the above described general process for the dimerization and trimerization of conjugated dienes is available when the electron donor Lewis base is a triaryl phosphite.

It has been found very surprisingly that when using triaryl phosphites as electron donors the mole ratio of these donors to the nickel compound as the compound of the transition metal cannot be varied at will but must be not higher than 4:1 and preferably from 2:1 to 1:1 to obtain high conversions of butadiene with high yields of cyclooctadi-1,5-ene in short reaction periods. If the mole ratio is increased to more than 4:1, the conversion is reduced very considerably as may be seen from Example 97.

It is also possible when using the specific electron donors of the invention to operate in the presence of solvents which are not reactive with the catalysts. However, advantageous operation without the use of a special solvent is possible by adding initially an appropriate amount of the main product produced by the reaction, e.g. cyclooctadi-1,5-ene, as a diluent. It is avoided in this manner that larger amounts of a solvent must be separated when processing the reaction product.

The process of the invention may be carried out under both atmospheric pressure and superatmospheric pressures, e.g. under pressures of 1 to 200 atmospheres. However, it is preferred to operate in pressure range of from 1 to 50 atmospheres. The reaction temperature preferably range between 0° and 200° C., best results being obtained in a temperature range between 70° and 140° C. The process may be carried out discontinuously, but continuous operation is also possible and advantageous.

The compounds obtained by the process of the invention are valuable starting products for further synthesis reactions; for example, cyclooctadi-1,5-ene may be used for obtaining suberic acid or the corresponding 9-membered lactam.

In order that the invention may be further understood, the following examples are given by ay of illustration only:

EXAMPLE 93

0.753 Gms. = 2.43 millimoles of triphenyl phosphite are dissolved in 15 ml. of benzene and the solution is saturated with butadiene. The solution is then mixed with 0.334 gms. = 1.2 millimoles of bis-cyclooctadi-1,5-ene-nickel-(O), which results in a red catalyst solution. Saturation of the solution with butadiene is repeated after 1 day and after 2 days. After 5 days, 3.57 grams of the butadiene are reacted. The reaction product contains 0.32 gms. = 8.9% of vinyl cyclohexene, 3.18 gms. = 89.2% of cyclooctadi-1,5-ene and 0.07 gms. = 1.9% of all trans-cyclododecatri-1,5,9-ene in addition to traces of higher polymers.

EXAMPLE 94

0.625 Gms. = 2.02 millimoles of triphenyl phosphite are dissolved in 15 ml. of benzene. The solution is mixed with 0.278 gms. = 1.01 millimoles of bis-cyclooctadi-1,5-ene-nickel-(O). After several minutes, precipitation of a minor amount of metallic nickel is observed. After 24 hours, the solution is saturated with butadiene and then treated as described in Example 1. After 7 days, there are obtained 4.19 gms. of a reaction product which contains 0.46 gms. = 11% of vinyl cyclohexene, 3.70 gms. = 88% of cyclooctadi-1,5-ene and 0.03 gms. = 0.8% of all trans-cyclododecatriene in addition to traces of higher polymers.

EXAMPLE 95

0.497 Gms. = 1.81 millimoles of bis-cyclooctadi-1,5-ene-nickel-(O) are dissolved together with 1.13 gms. = 3.62 millimoles of triphenyl phosphite in 20 ml. of benzene and the solution is immediately drawn by suction into an evacuated 200 ml. autoclave of stainless steel. 45 Gms. of butadiene are introduced under pressure and the autoclave is heated to 80° C. After 2 hours of reaction, 39 gms. of a reaction product (87% conversion) containing 4.2 gms. = 10.8% of vinyl cyclohexene, 33.6 gms. = 86.1% of cyclooctadi-1,5-ene and 0.7 gms. = 1.8% of all-trans-cyclododecatriene in addition to 0.5 gms. = 1.2% of higher polymers are obtained.

EXAMPLE 96

20.8 gms. = 45.2 millimoles of tri-α-naphthyl phosphite are dissolved together with 5.8 gms. = 22.6 millimoles of nickel acetylacetonate in a mixture of 85 gms. cyclooctadi-1,5-ene and 15 gms. of butadiene. The mixture is cooled with water and mixed with 5.9 gms. = 42.2 millimoles of ethoxy diethyl aluminum. The catalyst solution of orange color is introduced by suction into an evacuated 2 liter autoclave of stainless steel equipped with a magnetic stirrer. Butadiene in amount of 200 gms. is introduced under pressure and the autoclave is heated to 85° C. The temperature in the interior rises to 115° C. due to the reaction heat. The supply of external heat is stopped and after about 15 minutes the pressure has dropped to 3 atmospheres. Additional butadiene is now introduced under pressure at a rate sufficient to maintain the temperature in the interior between 110° and 115° C. In doing so, the pressure does not rise beyond 4 atmospheres. 1185 gms. of butadiene are injected within 1.5 hours. After a total of 1.75 hours of reaction time, 1249 gms. of a reaction product (89% conversion) containing 102 gms. = 8.2% of vinyl cyclohexene, 1128 gms. = 90.2% of cycloootadi-1,5-ene and 5.7 gms. = 0.5% of all trans-cyclododecatriene in addition to 13.4 gms. = 1.1% of higher polymers are obtained.

EXAMPLE 97

The reaction is carried out continuously in the following manner: The reactor used is a copper capillary of 100 meters in length and 4 mm. in inside diameter which is wound upon itself and placed in an oil bath heated to 120° C. Both a benzenic catalyst solution and liquid butadiene are injected into the heated capillary by means of two injection pumps. Arranged at the end of the reactor is a relief valve set at 30 atmospheres and releasing the product which is obtained at a rate corresponding to the output of the two pumps to atmospheric pressure. The ratio of catalyst rate to butadiene rate is preferably such that the butadiene is reacted to the greatest extent possible with a residence time of 1 hour.

The following test data illustrate the process:

Reaction of nickel acetylacetonate with ethoxy diethyl aluminum in the presence of triphenyl phosphite and small amounts of butadiene results in the formation of a catalyst solution in benzene, which contains 1 gram of nickel in 200 ml. of solution. A Ni:P:Al mole ratio of 1:2:2 is selected.

Within 50 minutes, 330 ml. of catalyst solution and 500 gms. of butadiene are injected into the reactor. Following this, 1 liter of additional benzene is pumped into the reactor thereby discharging the entire reaction product. There are obtained 490 gms. of a reaction product (98% conversion) which contains 1.1 gms. = 0.2% of 5-methyl heptatri-1,3,6-ene, 58.4 gms. = 11.9% of vinyl cyclohexene, 399 gms. = 81.4% of cyclooctadi-1,5-ene, 16.5 gms. = 3.4% of all trans-cyclodedecatriene and 4.4 gms. = 0.9% of trans, trans,-cis-cyclododecatriene in addition to 10.7 gms. = 2.2% of higher polymers. 400 gms. of butadiene/gm. of nickel/hr. are reacted with a 98% conversion.

When a 1:4 ratio of nickel to triphenyl phosphite is used and 250 ml. of catalyst solution and 440 gms. of butadiene are injected within 40 minutes with otherwise unchanged conditions, then 117.3 gms. of a reaction product (27% conversion) containing 22.8 gms. = 19.4% of vinyl cyclohexene, 85.7 gms. = 73% of cyclooctadi-1,5ene, 1.4 gms. = 1.2% of all trans-cyclododecatriene in addition to 7.4 gms. = 6.3% of higher polymers are obtained. Only 150 gms. of butadiene/gram of nickel/hour are reacted with an only 27% conversion.

If, under otherwise identical conditions, a 1:6 ratio of nickel to triphenyl phosphite is used and 350 ml. of catalyst solution and 500 gms. of butadiene are injected within 50 minutes, then 19.8 gms. of a reaction product (4% conversion) containing 5.5 gms. = 27.8% of vinyl cyclohexene, 13.75 gms. = 69.5% of cyclooctadi-1,5-ene and 0.55 gms. = 2.8% of higher polymers are obtained. Only 15 gms. of butadiene/gram of nickel/-hour are reacted with an only 4% conversion.

EXAMPLE 98

The procedure is the same as in Example 97 except that the temperature is 150° C. and a 1:2 mole ratio of nickel to triphenyl phosphite is used. Within 30 minutes, 220 ml. of catalyst solution and 305 gms. of butadiene are injected. There are obtained 304 gms. of a reaction product (100% conversion) which contains 38.8 gms. = 12.8% of vinyl cyclohexene, 239.3 gms. = 78.7% of cyclooctadi-1,5-ene, 11.6 gms.= 3.8% of all trans-cyclododecatriene, 1.3 gms. = 0.4% of trans,-trans,cis-cyclododecatriene, 12.9 gms. = 4.2% of higher polymers. With a substantially qunatitative conversion, 600 gms. of butadiene are reacted per gram of nickel per hour.

EXAMPLE 99

The procedure is the same as in Example 97 except that triguaiacyl phosphite is used as the donor, the mole ratio of nickel to donor being 1:2. The temperature used is 100° C. Within 1.5 hours, 590 ml. of catalyst solution and 900 gms. of butadiene are injected. There are obtained 740 gms. of a reaction product (82% conversion) which contains 53.9 gms. = 7.3% of vinyl cyclohexene, 672.0 gms. = 91% of cyclooctadi-1,5-ene, 6.2 gms. = 0.8% of all-trans-cyclododecatriene and 7.7 gms. = 1.0% of higher polymers. 200 gms. of butadiene/gram of nickel/hour are reacted with a 82% conversion.

EXAMPLE 100

The procedure is the same as in Example 97 except that tri-(o-oxy-diphenyl)-phosphite is used as the donor, the ratio of donor to Ni being 1:1. The temperature used is 80° C. Within 25 minutes, 340 ml. of catalyst solution and 560 gms. of butadiene are injected. There are obtained 403 gms. of a reaction product (72% conversion) which contains 15.4 gms. = 3.8% of vinyl cyclohexene, 384 gms. = 95.4% of cyclooctadiene and 3.2 gms. = 0.8% of higher polymers. At a 72% conversion, butadiene is reacted at a rate of 500 gms./gram of nickel/hr.

EXAMPLE 101

The procedure is the same as in Example 100 except that the temperature used is 120° C. Within 27 minutes, 330 ml. of catalyst solution and 800 gms. of butadiene are injected. There are obtained 647 gms. of a product (81% conversion) which contains 32.7 gms. = 5.1% of vinyl cyclohexene, 598 gms. = 92.5% of cyclootadiene and 16.4 gms. = 2.5% of cyclododecatriene. With a 81% conversion, butadiene is reacted at a rate of 870 gms./gm. of nickel/hr.

EXAMPLES 102 and 105

The procedure is the same as in Example 97 except that the temperature used is 120° C. and the mole ratio of nickel to donor is varied. The donor used in triguaiacyl phosphite.

In the following tables, VCH means vinyl cyclohexene, COD means cyclooctadi-1,5-ene, and CDT means cyclododecatri-1,5,9-ene.

| Example | Ni: donor | % Conversion | % VCH | % COD | % CDT | % cyclic hydrocarbons | % polymers | gms. butadiene g.Ni/hr. |
|---|---|---|---|---|---|---|---|---|
| 102 | 110.5 | 48 | 7.9 | 82.7 | 8.7 | 99.3 | 0.7 | 410 |
| 103 | 111 | 90 | 7.0 | 85.3 | 6.1 | 98.4 | 1.6 | 930 |
| 104 | 112 | 98 | 6.8 | 89.2 | 2.4 | 98.4 | 1.6 | 670 |
| 105 | 114 | 93 | 10.2 | 88.3 | 1.4 | 99.9 | — | 230 |

EXAMPLES 106 to 108

The procedure is the same as that described in Example 104 except that the nickel salt is reduced with different organic aluminum compounds.

| Example | Ni:Al | Reducing agent | % conversion | % VCH | % COD | % CDT | % polymers | g.butadiene g.Ni/ hr. |
|---|---|---|---|---|---|---|---|---|
| 106 | 1:1 | Al(i-C₄H₉)₃ | 80 | 6.5 | 89.5 | 2.3 | 1.3 | 650 |
| 107 | 1:1 | Al(C₂H₅)₃ | 82 | 8.1 | 88.4 | 2.5 | 1.0 | 660 |
| 108 | 1:1 | HAl(C₂H₅)₂ | 21 | 9.8 | 76.2 | trace | 14.0 | 110 |

EXAMPLES 109 to 111

The procedure in care of Examples 109 to 110 is the same as in Example 104 except that the temperature used is 80° C. and the relief valve of the reactor is set at different pressures. The procedure in Example 111 is the same as in Example 112.

| Example | Pressure atm. | % conversion | % VCH | % COD | % CDT | % polymers | g.butadiene/ g.Ni/hr. |
|---|---|---|---|---|---|---|---|
| 109 | 150 | 51 | 6.8 | 91.7 | 1.5 | — | 300 |
| 110 | 35 | 90 | 7.1 | 92.3 | trace | 0.7 | 290 |
| 111 | 1 | 99 | 7.1 | 92.3 | — | 0.7 | 300 |

EXAMPLES 112 to 114

The reaction is carried out at atmospheric pressure in the following manner: A catalyst solution in cyclooctadiene, containing 1 gm. of nickel per 100 ml. of solution, is prepared by reduction of nickel acetylacetonate with ethoxy diethyl aluminum in the presence of triaryl phosphite and small amounts of butadiene. A 1:1:2 mole ratio of Ni-donor:Al is used. The three possible tri-monomethoxy-phenyl phosphites are used as the donors. The catalyst solution contained in a flask equipped with a thermometer, stirrer and an inlet pipe is heated at 80° C. while introducing butadiene and vigorously stirred at this temperature.

| Example | Position of OCH₃ group | % VDH | % COD | % CDT | % polymers | gms. butadiene/ gm.Ni/hr. |
|---|---|---|---|---|---|---|
| 112 | ortho | 6.0 | 91.3 | 1.6 | 1.1 | 300 |
| 113 | meta | 7.5 | 83.3 | 9.3 | — | 140 |
| 114 | para | 10.1 | 78.6 | 9.6 | 1.8 | 90 |

All of the three experiments were carried out for 3 hours.

EXAMPLE 115

The procedure is the same as in Example 112 except that tri-(ortho oxydiphenyl)-phosphite is used as the donor. The butadiene charged is dried by means of organometallic compounds. 7.42 kgs. of butadiene are reacted with 1.12 gms. Ni within 9 hours. 5.53 kgs. of product are distilled off at 14 mm. Hg. Additional butadiene was introduced at 80° C. into the remaining solution. Additional 4.97 kgs. of butadiene were reacted during the course of 7 hours. The following rates of conversion were determined by means of a calibrated rotameter:

| | |
|---|---|
| Beginning of 1st batch: | 810 gms. butadiene/gm. Ni/hr. |
| After 9 hours: | 655 gms.butadiene/gm. Ni/hr. = 81% of initial activity |

What is claimed is:

1. As a novel complex compound, dicyclooctadiene-nickel of the formula $(C_8H_{12})_2Ni$ in the form of yellow crystals.

2. As a novel complex compound, cyclooctatetraene-nickel of the formula $C_8H_8Ni$ in the form of black-colored needles having metallic lustre.

3. As a novel complex compound, all-trans-cyclododeca-(1,5,9)-triene-centro-nickel in the form of pure red crystals.

4. As a novel complex compound, cyclooctadiene-nickel-acetylacetone of the formula $C_{13}H_{20}O_2Ni$ in the form of orange-colored crystals.

5. As a novel complex compound, tris(stilbene) nickel of the formula $Ni(C_{14}H_{12})_3$ in the form of brown crystals.

6. As a novel complex compound, a member of the group consisting of cobalt cyclooctatetraene and cobalt bis(cyclooctatetraene) represented by the formula $CO(C_8H_8)_x$ in the form of a dark-brown powder, wherein $x$ is, respectively, 1 or 2.

* * * * *

UNITED STATES PATENT AND TRADEMARK OFFICE
CERTIFICATE OF CORRECTION

PATENT NO. : 4,017,526
DATED : April 12, 1977
INVENTOR(S) : Gunter Wilke and Ernst Willi Muller It is certified that error appears in the above-identified patent and that said Letters Patent are hereby corrected as shown below:

| | |
|---|---|
| Column 2, line 41, delete and insert therefor | "camium" --osmium-- |
| Column 2, line 44, delete and insert therefor | "he" --the-- |
| Column 2, line 56, delete and insert therefor | "araines" --arsines-- |
| Column 4, line 27, delete and insert therefor | "in" --is-- |
| Column 6, line 37, delete and insert therefor | "wit" --with-- |
| Column 6, line 63, delete and insert therefor | "butadiene" --crystals-- |
| Column 7, line 61, delete and insert therefor | "2.5" --20.5-- |
| Column 8, line 20, delete and insert therefor | "$Ti_1$" --$Ti_2$-- |
| Column 9, line 7, delete and insert therefor | "$(P(C_6H_5)_3)$" --$(P(C_6H_5)_3)_2$-- |
| Column 9, line 48, delete and insert therefor | "1,5,9-one" --1,5,9-ene-- |

UNITED STATES PATENT AND TRADEMARK OFFICE
CERTIFICATE OF CORRECTION

PATENT NO. : 4,017,526
DATED : April 12, 1977
INVENTOR(S) : Gunter Wilke and Ernst Willi Muller It is certified that error appears in the above-identified patent and that said Letters Patent are hereby corrected as shown below:

Column 10, line 50, delete "disslved" and insert therefor --dissolved--

Column 10, line 55, delete "bitadiene" and insert therefor --butadiene--

Table I, at Column 11, Temp/Conversion delete "80°" (next to last) and insert therefor --60°--

Table II, at Column 11, fourth column head, delete "Cycloocta-di-,5-ene" and insert therefor --Cycloocta-di-1,5-ene--

Table II, at Column 11, seventh column head, delete "Non volatile functions" and insert therefor --Non volatile fractions--

Table IV, at Column 13, second column, delete "(A)", both occurrences, and insert therefor --(A)--

Column 14, line 10, delete "othoxy" and insert therefor --ethoxy--

Table V, at Column 14, delete the footnote "(1)" at column 7 and reinsert it at last column

UNITED STATES PATENT AND TRADEMARK OFFICE
CERTIFICATE OF CORRECTION

PATENT NO. : 4,017,526
DATED : April 12, 1977
INVENTOR(S) : Gunter Wilke and Ernst Willi Muller It is certified that error appears in the above-identified patent and that said Letters Patent are hereby corrected as shown below:

Column 17, line 39, insert --a-- before "pressure"

Column 17, line 53, delete "ay"
and insert therefor --way--

Column 20, line 2, delete "qunatitative"
and insert therefor --quantitative--

Column 20, line 47, delete "in"
and insert therefor --is--

Table at Column 20, second
column thereof headed
"Ni:Donor" delete the second numeral "1"
and insert therefor --:-- (a colon)

Column 21, line 12, delete "care"
and insert therefor --case--

Column 21, line 12, delete "to"
and insert therefor --and--

Column 21, line 34, delete "Ni-donor"
and insert therefor --Ni:donor--

UNITED STATES PATENT AND TRADEMARK OFFICE
CERTIFICATE OF CORRECTION

PATENT NO. : 4,017,526
DATED : April 12, 1977
INVENTOR(S) : Gunther Wilke and Ernst Willi Muller It is certified that error appears in the above-identified patent and that said Letters Patent are hereby corrected as shown below:

Column 1, lines 17, 20, 26, 29, 38, 42, 43, 47 and 51, in each instance, "II" should read $--\pi$ Column 2, lines 13, 21 and 37, in each instance, "II" should read $--\pi$ Column 3, line 60, "II" should read $--\pi$ Column 9, line 11 "II" should read $--\pi$ Signed and Sealed this Twenty-first Day of February 1978

[SEAL]

Attest:

RUTH C. MASON
*Attesting Officer*

LUTRELLE F. PARKER
*Acting Commissioner of Patents and Trademarks*